United States Patent
Habets et al.

(10) Patent No.: US 8,631,025 B2
(45) Date of Patent: Jan. 14, 2014

(54) FILTER BY EXAMPLE

(75) Inventors: Raymond Joseph Elisabeth Habets, Eindhoven (NL); Rutger Nijlunsing, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 122 days.

(21) Appl. No.: 12/516,662

(22) PCT Filed: Nov. 26, 2007

(86) PCT No.: PCT/IB2007/054780
§ 371 (c)(1),
(2), (4) Date: Jan. 13, 2010

(87) PCT Pub. No.: WO2008/065593
PCT Pub. Date: Jun. 5, 2008

(65) Prior Publication Data
US 2010/0121846 A1    May 13, 2010

(30) Foreign Application Priority Data

Nov. 29, 2006  (EP) .................................. 06124988

(51) Int. Cl.
*G06F 17/30*    (2006.01)
(52) U.S. Cl.
USPC .......................... 707/759; 707/765; 707/772
(58) Field of Classification Search
USPC .......... 707/729, 730, 726, 748, 749, 737, 736
See application file for complete search history.

(56) References Cited

U.S. PATENT DOCUMENTS

| 7,043,474 B2* | 5/2006 | Mojsilovic et al. ................... 1/1 |
| 7,212,311 B2* | 5/2007 | Takamori et al. ............... 358/1.9 |
| 7,478,091 B2* | 1/2009 | Mojsilovic et al. .................... 1/1 |
| 7,907,755 B1* | 3/2011 | Perlmutter et al. ........... 382/118 |
| 7,916,976 B1* | 3/2011 | Kedikian ....................... 382/305 |
| 2001/0006425 A1* | 7/2001 | Takamori et al. ............. 358/530 |
| 2002/0174120 A1 | 11/2002 | Zhang et al. |
| 2003/0123737 A1* | 7/2003 | Mojsilovic et al. ........... 382/224 |

(Continued)

OTHER PUBLICATIONS

Lattanzi, R., et al.; Hip-Op: Innovative software to plan total hip replacement surgery; 2002; Medical Informatics and the Internet in Medicine; 27(2)abstract.

(Continued)

*Primary Examiner* — Sherief Bradawi

(57) ABSTRACT

The invention relates to a system (100) for identifying a certain data-object of a set of data-objects, wherein each data-object of the set of data-objects is described by a plurality of discriminating characteristics, the system comprising: a composition unit (110) for composing a query for identifying the certain data-object; an identification unit (120) for identifying a candidate data-object of the set of data-objects, based on the query; a presentation unit (130) for presenting a description of the candidate data-object to a user; a feedback unit (140) for receiving user feedback on a discriminating characteristic of the plurality of discriminating characteristics, the discriminating characteristic describing the candidate data-object; and an update unit (150) for updating the query for identifying the certain data-object, based on the user feedback on the discriminating characteristic describing the candidate data-object. Thus, the user may evaluate a discriminating characteristic of the candidate data-object, based on information obtained from the presentation unit, and provide user feedback comprising a reason specifying why the retrieved data is relevant and/or not relevant to the query.

20 Claims, 5 Drawing Sheets

(56) References Cited

U.S. PATENT DOCUMENTS

| | | | |
|---|---|---|---|
| 2003/0176783 A1* | 9/2003 | Hu | 600/429 |
| 2003/0195883 A1* | 10/2003 | Mojsilovic et al. | 707/6 |
| 2003/0212699 A1 | 11/2003 | Denesuk et al. | |
| 2004/0169673 A1 | 9/2004 | Crampe et al. | |
| 2004/0177069 A1* | 9/2004 | Li et al. | 707/5 |
| 2005/0055344 A1* | 3/2005 | Liu et al. | 707/3 |
| 2005/0189419 A1* | 9/2005 | Igarashi et al. | 235/454 |
| 2006/0036950 A1* | 2/2006 | Himberger et al. | 715/732 |
| 2006/0112092 A1* | 5/2006 | Ziou et al. | 707/5 |
| 2006/0142657 A1 | 6/2006 | Quaid et al. | |
| 2006/0143176 A1* | 6/2006 | Mojsilovic et al. | 707/6 |
| 2006/0156254 A1* | 7/2006 | Satake | 715/838 |
| 2006/0259360 A1* | 11/2006 | Flinn et al. | 705/14 |
| 2011/0298428 A1* | 12/2011 | Liu | 320/162 |

OTHER PUBLICATIONS

Sagbo, S., et al.; A semi-automatic orthopedic implant management tool for Computer Assisted planning, navigation and simulation: from XML implant database to unified implant access interface; 2005; IEEE Proc. Engineering in Medicine and Biology; pp. 890-893.

Glassman, A. H.; Preoperative planning for primary total hip arthroplasty; 1995; Operative Techniques in Orthopaedics; 5(4)296-305.

Kherfi, M. L., et al.; Relevance Feedback in Image Retrieval: A New Approach using Positive and Negative Examples; 2003; Proc. IS&T/SPIE conf. Internet Imaging; pp. 208-218.

Ghebreab, S., et al.; Concept-Based Retrieval of Biomedical Images; 2006; http:\\staff.science.uva.nl/-ghebreab/pdffiles/SMI2003Ghbreab.pdf.

Kherfi, M. L., et al.; Relevance Feedback for CBIR: A New Approach Based on Probabilistic Feature Weighting with Positive and Negative Examples; 2006; IEEE Trans. on Image Processing; 15(4)1017-1030.

Rui, Y., et al.; Relevance Feedback: A Power Tool for Interactive Content-Based Image Retrieval; 1998; IEEE Trans. on Circuits and Systems for Video Technology; 8(5)644-655.

Wu, H., et al.; Willhunter: Interactive Image Retrieval with Multilevel Relevance Measurement; 2004; IEEE Trans. on Conf. on Pattern Recognition; 4 pages.

Nakazato, M., et al.; Evaluatiing Group-Based Relevance Feedback for Content-Based Image Retrieval; 2003; IEEE Trans. on Image Processing Conf.; vol. 2; pp. 599-602.

\* cited by examiner

FIG. 2

CLS 145 Stem
Why do you want to reject this template?
Please select one reason, and add to filter.

Current template
Offset          23mm
CCD angle       120
Leg length difference 5mm Too small for shaft,
Filter
5 templates.

CCD angle too small,
Filter
4 templates.

Offset is too small,
Filter
7 templates.

Too large for shaft,
Filter
8 templates.

CCD angle too large,
Filter
this template.

Offset is too large,
Filter
13 templates.

No reason
Filter
this template.

Cancel

FILTER BY EXAMPLE

FIELD OF THE INVENTION

The invention relates to the field of medical data storage and retrieval and more specifically to medical data retrieval employing user feedback.

BACKGROUND OF THE INVENTION

A system for image retrieval is described in an article by Y. Rui, et al, entitled "Relevance Feedback Techniques in Interactive Content-based Image Retrieval," in Proc. IS&T and SPIE Storage and Retrieval of Image and Video Databases VI, San Jose, Calif., USA, January 1998, pages 25-36, hereinafter referred to as Ref. 1. In the relevance feedback approach the user provides feedback on a retrieved image to the system. First, the system is arranged to retrieve images from a collection of images, based on a query image, by comparing predetermined features of the query image to the respective features of each image of the collection of images. Second, the user ranks retrieved images according to their resemblance to the query image in the view of the user. This ranking is called "relevance feedback". The relevance feedback is then used to compute optimal weights of features used for identifying images for retrieval, and hence to determine relevant features. The features and their weights define a new similarity measure, suitable for the query image or for a family of similar query images. The new similarity measure may be used for retrieving an image from the collection of images, based on a query image of the family of query images.

SUMMARY OF THE INVENTION

A limitation of the image retrieval method described in Ref. 1 is that the user feedback is based on ranking a retrieved image according to its relevance to the query image. However, the user feedback does not include a reason specifying why the retrieved image is relevant to the query image, i.e. the user cannot specify which feature makes the retrieved image relevant to the query image. Moreover, the system uses low-level computer-oriented features, which can be easily computed based on the image data, while the user prefers high-level human-oriented features, which are based on human perception.

It would be advantageous to have a system for retrieving data from a set of data, which system is capable of obtaining and using user feedback comprising a reason specifying why the retrieved data is relevant and/or not relevant to the query. This method is intuitive from a user viewpoint.

To address this concern, in an aspect of the invention, a system for identifying a certain data-object of a set of data-objects, wherein each data-object of the set of data-objects is described by a plurality of discriminating characteristics, comprises:

a composition unit for composing a query for identifying the certain data-object;

an identification unit for identifying a candidate data-object of the set of data-objects, based on the query;

a presentation unit for presenting a description of the candidate data-object to a user;

a feedback unit for receiving user feedback on a discriminating characteristic of the plurality of discriminating characteristics, the discriminating characteristic describing the candidate data-object; and an update unit for updating the query for identifying the certain data-object, based on the user feedback on the discriminating characteristic describing the candidate data-object.

A data-object of the set of data-objects may comprise data such as, but not limited to, a brain image data or an image data showing a stent for placement in a coronary artery, or a graph of a coronary artery tree. Each data-object is described by a plurality of discriminating characteristics. For example, the brain image data may be described by the size of a brain tumor, the location of the brain tumor, and the average intensity of the brain tumor, e.g. in Hounsfield units for a CT brain image data. The stent image data may be described by the stent length, diameter, and elasticity. The graph of a coronary artery tree may be described by the graph vertices and edges.

A description of the candidate data-object identified by the identification unit, based on the query composed by the composition unit, is presented to the user by the presentation unit. For example, the presentation unit may be arranged to display a view of the identified brain image data. The user may evaluate a discriminating characteristic of the candidate data-object, based on information obtained from the presentation unit, and provide user feedback. For example, the user feedback on the identified brain image data may comprise information that the size of the tumor in the displayed image is too small, that the location of the tumor is all right, and that the average intensity of the tumor should be higher than the average intensity of the tumor in the identified brain data. The update unit is arranged to update the query, based on the user feedback. Thus, the system of the invention is arranged for obtaining and using user feedback comprising a reason specifying why the retrieved data is relevant and/or not relevant to the query.

In an embodiment of the system, the feedback unit is further arranged for requesting the user feedback on the discriminating characteristic describing the candidate data-object. Requesting the user for feedback on the discriminating characteristic of the candidate data-object helps the user provide syntactically and semantically correct user feedback relevant to the discriminating characteristic of the candidate data-object.

In an embodiment of the system, the system further comprises a reference unit for receiving a reference data-object. The identified candidate data-object may be compared to the reference data-object. For example, a graphic representation of the candidate data-object such as a stent and of the reference data-object such as a coronary artery may be displayed by the system and shown to the user. The user feedback may be advantageously based on the reference data-object. This may make it easier for the user to provide feedback on the identified candidate data-object.

In an embodiment of the system, the system further comprises a registration unit for registering the candidate data-object with the reference data-object. The registration may be interactive and/or automatic. Registering the candidate data-object with the reference data-object may further make it easier for the user to determine feedback. For example, placing a stent image in a view of the coronary artery may help the user to determine feedback on the length of the stent.

In an embodiment of the system, the system further comprises a computation unit for computing a value of a parameter describing the candidate data-object. Computing a value of a parameter describing the candidate data-object may further make it easier for the user to determine feedback. For example, the computation unit may be arranged to compute recommended stent elasticity. The computation may be based on the curvature of a fragment of the artery, with which the stent is registered.

In an embodiment of the system, the set of data-objects is a set of implant data-objects. There may be many applications of the system of the invention. Using the system of the invention to facilitate the selection of an implant for a patient, e.g. an orthopedic implant such as a hip implant, may significantly shorten the time required to find an implant suitable for the patient.

In an embodiment of the system, the set of data-objects is a set of image data-objects. Retrieving an image describing a known case similar to a current case studied by a physician may provide important clues about the current case. The system of the invention is intuitive in use and capable of shortening the time required to find a case relevant to the current case.

It is appreciated that any two or more of the above-mentioned embodiments of the system may be combined in any useful way.

In a further aspect of the invention, the system according to the invention is comprised in an image acquisition apparatus.

In a further aspect of the invention, the system according to the invention is comprised in a workstation.

In a further aspect of the invention, a method of identifying a certain data-object of a set of data-objects, wherein each data-object of the set of data-objects is described by a plurality of discriminating characteristics, comprises:

a composition step for composing a query for identifying the certain data-object;

an identification step for identifying a candidate data-object of the set of data-objects, based on the query;

a presentation step for presenting a description of the candidate data-object to a user;

a feedback step for receiving user feedback on a discriminating characteristic of the plurality of discriminating characteristics, the discriminating characteristic describing the candidate data-object; and an update step for updating the query for identifying the certain data-object, based on the user feedback on the discriminating characteristic describing the candidate data-object.

In a further aspect of the invention, a computer program product to be loaded by a computer arrangement comprises instructions for identifying a certain data-object of a set of data-objects, wherein each data-object of the set of data-objects is described by a plurality of discriminating characteristics, the computer arrangement comprising a processing unit and a memory, the computer program product, after being loaded, providing said processing unit with the capability to carry out the tasks of:

composing a query for identifying the certain data-object;

identifying a candidate data-object of the set of data-objects, based on the query;

presenting a description of the candidate data-object to a user;

receiving user feedback on a discriminating characteristic of the plurality of discriminating characteristics, the discriminating characteristic describing the candidate data-object; and updating the query for identifying the certain data-object, based on the user feedback on the discriminating characteristic describing the candidate data-object.

Modifications and variations of the image acquisition apparatus, of the workstation, of the method, and/or of the computer program product, which correspond to the described modifications and variations of the system, can be carried out by a skilled person on the basis of the present description.

BRIEF DESCRIPTION OF THE DRAWINGS

These and other aspects of the invention will become apparent from and will be elucidated with respect to the implementations and embodiments described hereinafter and with reference to the accompanying drawings, wherein:

FIG. 2 shows a snapshot of an exemplary hip-implant template dialog;

The same reference numerals are used to denote similar parts throughout the Figures.

DETAILED DESCRIPTION OF EMBODIMENTS

Figure 1:
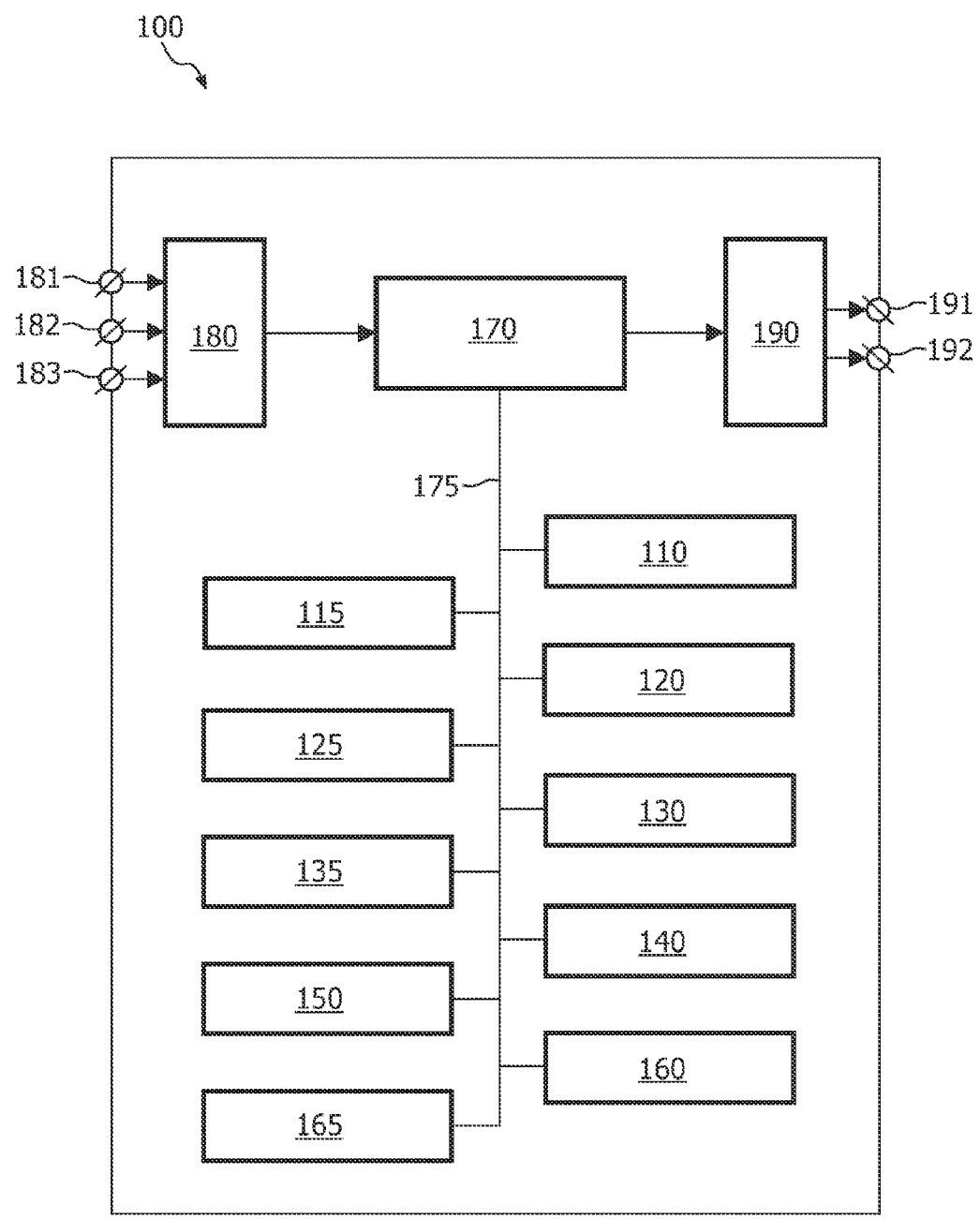
FIG. 1 schematically shows a block diagram of an exemplary embodiment of the system.

FIG. 1 schematically shows a block diagram of an exemplary embodiment of the system 100 for identifying a certain data-object of a set of data-objects, wherein each data-object of the set of data-objects is described by a plurality of discriminating characteristics, the system 100 comprising:

a composition unit 110 for composing a query for identifying the certain data-object;

an identification unit 120 for identifying a candidate data-object of the set of data-objects, based on the query;

a presentation unit 130 for presenting a description of the candidate data-object to a user;

a feedback unit 140 for receiving user feedback on a discriminating characteristic of the plurality of discriminating characteristics, the discriminating characteristic describing the candidate data-object; and an update unit 150 for updating the query for identifying the certain data-object, based on the user feedback on the discriminating characteristic describing the candidate data-object.

The exemplary embodiment of the system 100 further comprises the following optional units:

a reference unit 115 for receiving a reference data-object;

a registration unit 125 for registering the candidate data-object with the reference data-object;

a computation unit 135 for computing a value of a parameter describing the candidate data-object;

a control unit 160 for controlling the workflow in the system 100;

a user interface 165 for communicating with the user of the system 100; and a memory unit 170 for storing data.

In an embodiment of the system 100, there are three input connectors 181, 182 and 183 for the incoming data. The first input connector 181 is arranged to receive data coming in from data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to data storage means such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, a query data input and the reference data-object. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the identified data-object. The memory unit 170 is also arranged to receive data from and deliver data to the units of the system 100 comprising the composition unit 110, the reference unit 115, the identification unit 120, the registration unit 125, the presentation unit 130, the computation unit 135, the feedback unit 140, the update unit 150, the control unit 160, and the user interface 165, via a memory bus 175. The memory unit 170 is further arranged to make the output data available to external devices via any of the output connectors 191 and 192. Storing the data from the units of the system 100 in the memory unit 170 may advantageously improve the performance of the units of the system 100 as well as the rate of transfer of the output data from the units of the system 100 to external devices.

Alternatively, the system 100 may not comprise the memory unit 170 and the memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit may be arranged to receive control data from and provide control data to the units of the system 100. For example, after the identification of a candidate data-object, the computation unit 120 may be arranged to pass a control data "a candidate data-object is identified" to the control unit 160 and the control unit 160 may be arranged to provide a control data "display the candidate data-object" to the presentation unit 130, requesting the presentation unit 130 to display a view of the identified candidate data-object. Alternatively, a control function may be implemented in another unit of the system 100.

In an embodiment of the system 100, the system 100 comprises a user interface 165 for communicating with the user of the system 100. The user interface 165 may be arranged to prompt a user for user feedback on the identified candidate object. Optionally, the user interface may be arranged to receive a user input for selecting a mode of operation of the system 100 such as a mode for registering the identified candidate data-object with the reference data-object. A skilled person will understand that more functions may be advantageously implemented in the user interface 165 of the system 100.

The system 100 is arranged for identifying a certain data-object of a set of data-objects, each data-object of the set of data-objects being described by a plurality of discriminating characteristics. A data-object typically describes a physical object. For example, a data-object may comprise an image data set, each image data set comprising data for visualizing a physical object. The physical object described by the data object may be an anatomical structure such as heart, brain, lung, knee joint, vertebra, for example. The data-object may further comprise information on the physical object such as a patient's name and age, diagnosis, and location of the object, for example. The set of data-objects may have a structure. Exemplary structures of the set of data-objects include, but are not limited to, a linked list, a binary tree, a graph, and a relational database.

Each data-object is described by a plurality of discriminating characteristics. For example, a discriminating characteristic of a stent may be the stent length, a discriminating characteristic of a brain image may be a contour of a brain tumor, and a discriminating characteristic of a pair of image data sets comprising a 3D image data set of the heart at the diastole end and a 3D image data set of the heart at the systole end may be the ejection fraction. The plurality of discriminating characteristics may be comprised in the system, which may be designed for identifying a certain data-object of a particular type, for example, an image data, a medical implant, a stent, or a composition of a cream for skin rash treatment. Alternatively, the plurality of discriminating characteristics may be comprised in a data-object of the set of data objects.

The composition unit 110 of the system 100 is arranged for composing a query for identifying the certain data-object. The query may be based on a user input. The query will depend on the data-object stored in the set of data-objects. For example, in the case of a data-object comprising a medical image data set, the query may comprise name, age and sex of a patient, diagnosis, modality used to acquire the image data, e.g. thoracic CT scan, information when the image data was acquired, name of the family physician, etc. Each of these data-object components may be part of the query. The query may also comprise a value of a discriminating characteristic. The value may be a numerical value, e.g. the length of a stent, or a set of numerical values, e.g. coordinates of vertices describing a contour of a brain tumor.

The identification unit 120 of the system 100 is arranged for identifying a candidate data-object of the set of data-objects, based on the query. The identification unit 120 is arranged to select a data-object of the set of data-objects, and to evaluate the selected data-object of the set of objects, based on the query. If the data-object satisfies the query, the identification unit 120 identifies said data-object as a candidate data-object. The identification unit 120 may be arranged to select a further data-object and examine whether or not the selected data object satisfies the query. In an embodiment, the data-objects may be selected at random. In another embodiment, the set of data-objects may be organized in a binary tree and the identification unit may be arranged to traverse the binary tree. A skilled person will know various methods of traversing various data structures such as a linked list, a tree and a relational database, for example.

The identification unit 120 may be arranged to examine only part of the data-object comprised in the relevant component of the data object needed for evaluation based on the query. Optionally, the set of data-objects may be indexed. The index may comprise data for identifying the data-object. The identification unit 120 may be arranged to identify a data-object, based on the index of the data-object. This may accelerate the identification of a candidate data-object, especially in the case of a large data-object, e.g. an image of 10 Megabytes.

A skilled person will appreciate that the identification unit 120 may be arranged to identify a plurality of candidate data-objects which satisfy the query. If no data-object satisfies the query, the user interface 165 of the system 100 may be arranged to display a "failed" message, e.g. "no data-object satisfying criteria specified by the query has been found".

The presentation unit 130 of the system 100 is arranged for presenting a description of the candidate data-object to a user. For example, if the data-object comprises an image data, said image may be presented to the user. If the data object comprises a three-dimensional (3D) image data set, a computed view based on said 3D image data set may be presented to the user. Optionally, the user may be enabled to interactively select the view to be computed using the user interface 165. The presentation unit may be further arranged to present a value of a discriminating characteristic describing the candidate data object. Also, any further information describing the data-object, which is deemed useful, may be presented to the user.

The feedback unit 140 of the system 100 is arranged for receiving user feedback on a discriminating characteristic of the plurality of discriminating characteristics, the discriminating characteristic describing the candidate data-object. If the candidate data-object cannot be accepted by the user as the certain data-object, the user may determine, based on the description of the candidate data-object presented by the presentation unit 130, why the candidate data-object cannot be accepted. The feedback unit 140 is arranged to receive the user feedback for determining which discriminating characteristic of the identified candidate data-object does not satisfy user requirements. Further, the feedback unit 140 may be arranged to receive further user feedback on why the value of a discriminating characteristic describing the candidate data object is not good, e.g. whether the value of the discriminating characteristic of the certain data-object is greater than or smaller than the value of said discriminating characteristic of the candidate data-object. Alternatively, the user may provide the feedback unit 140 with feedback that the value of the discriminating characteristic is accepted. If the user accepts the value of a discriminating characteristic of the candidate data-object, the candidate data-object may be accepted by the system 100 as the certain data-object.

In an embodiment of the system 100, the feedback unit 140 is further arranged for requesting user feedback on the discriminating characteristic describing the candidate data-object. For example, the feedback unit 140 may be arranged to employ the user interface 165 for displaying a dialog comprising a feedback query on the discriminating characteristic of the candidate data-object. The feedback query may be comprised in the system 100 or may be comprised in the candidate data-object identified by the identification unit 120, for example. The dialog may further display means for receiving user feedback, e.g. a toggle button, a checkbox, a text box, a slider, and/or a list of alternatives to select from. Alternatively, a text-based dialog may be arranged to display queries and to accept a syntactically correct user input.

In an embodiment of the system 100, the system 100 further comprises a reference unit 115 for receiving a reference data-object. The presentation unit 130 may be arranged to present a description of the reference data-object and of the candidate data-object to the user. The user may compare the description of the reference data-object and of the candidate data-object. The comparison of the two descriptions can make it easier for the user to determine the feedback. The reference data-object may be a data-object deemed similar to the certain data-object. Alternatively, the reference data-object may be a data-object deemed complementary to the certain data-object. Optionally, the reference data-object may be used by the composition unit 110 for extracting information for composing a query, e.g. for computing an initial range of values of a discriminating characteristic.

In an embodiment of the system 100, the system 100 further comprises a registration unit 125 for registering the candidate data-object with the reference data-object. The registration method implemented in the registration unit 125 may be automatic, semi-automatic, or manual. Registering the candidate data-object with the reference data-object further assists the user in providing useful user feedback to the feedback unit 140.

In an embodiment of the system 100, the system 100 further comprises a computation unit 135 for computing a value of a parameter describing the candidate data-object. For example, a parameter describing a data-object comprising an image may be the image histogram. The computation unit 135 may be arranged to compute the histogram of the image and the presentation unit may present the histogram to the user. In an embodiment of the system 100, the computation unit 135 may be arranged to compute the root-mean-square error based on the histogram of the image comprised in the candidate data-object and on the histogram of a reference image comprised in a reference data-object. In an embodiment of the system 100, the computation unit 135 may be arranged to compute the percentage to which an occluded part of an artery is opened by a stent placed in the artery based on an image of said artery registered with an image of said stent. Optionally, the computed value of the parameter describing the candidate data-object may be the value of a discriminating characteristic describing the candidate data-object.

In an embodiment of the system 100, the value of a discriminating characteristic of the plurality of discriminating characteristics is based on a data-object of the set of data-objects and the reference data-object. For example, each data-object may comprise a hip-implant template describing a hip-implant and the reference data-object may comprise an image of the legs of a patient needing a hip implant. The identification unit 120 is arranged to find a candidate data-object—a hip-implant template. The registration unit 125 may be arranged to register the candidate hip-implant template with the image of the patient and/or the computation unit 135 may be arranged to compute a difference in leg lengths based on the hip implant and on the image of the patient. Alternatively, an image of the candidate hip-implant template registered with the image of the patient may be displayed by the presentation unit 130. Different hip implants may result in different leg length differences. If the leg length difference is too large, the candidate hip implant may be unacceptable. The leg length difference may be used by the system 100 as a discriminating characteristic of hip implants.

The update unit 150 of the system 100 is arranged for updating the query for identifying the certain data-object, based on the user feedback on the discriminating characteristic describing the candidate data-object. The feedback unit 140 and, optionally, the reference unit 115, the registration unit 125 and the computation unit 135, allow updating said query in an intuitive way based on user perception and evaluation of the candidate data-object.

In an embodiment of the system 100, the set of data-objects is a set of implant data-objects. For example, the set of data-objects is a set of hip-implant templates. The plurality of discriminating characteristics describing a hip-implant template comprises an offset, a shaft size and a change of the collodiaphyseal (CCD) angle. The query composed by the composition unit may be based upon measurements of the non-involved side of the patient, initial measurements of the fit based on the patient's anatomy, and, optionally, on initial ranges of values of the discriminating characteristics. Based on the query, a list of candidate best fitting hip-implants is presented to the user, e.g. an orthopaedic surgeon. The list may further comprise a list of characteristics of respective hip implants. Optionally, a tiled set of images showing individual implants may be displayed. A contour of the hip-implant template may be superposed over an image of the patient's hip. The user may provide feedback based on said list of candidate best fitting implants and their characteristics and/or based on the displayed images. The feedback unit 140 may comprise a textual or a graphical dialog. If the user discards a hip-implant template from the list of best fitting hip implants, a dialog may be displayed and the user may be asked to enter feedback comprising information on a discriminating characteristic, i.e why the hip-implant represented by the hip-implant template is to be discarded.

FIG. 2 shows a snapshot of an exemplary hip-implant template dialog. The candidate CLS 145 Stem hip implant is to be discarded. The dialog comprises a first region 210 for displaying values of the discriminating characteristics of the candidate hip implant and a second region 215 for displaying a view of the candidate hip implant. The dialog further comprises filter buttons for obtaining user feedback on why the hip implant is to be discarded. If a button is pressed, the query is updated accordingly. For example, if the "Too small for shaft" button 221 is pressed, the query will be updated by the update unit 150, based on this feedback. The updated query will comprise an instruction for the identification unit 120 to limit identifying the hip-implant templates to hip-implants larger than the presented candidate hip-implant. In yet another example, if the "Offset is too large" button 227 is pressed, the updated query will comprise an instruction for the identification unit 120 to limit identifying the hip-implant templates to hip-implants with an offset smaller than the offset of the candidate hip-implant.

In the embodiment shown in FIG. 2, each filter button region comprises the name of the button stating a reason for rejecting the candidate template, i.e. defining a discriminating characteristic associated with the button, a graphical representation of the reason, the filter button, and the number of hip-implant templates in the set of hip-implant templates which will be considered by the identification unit 120 if the filter button is pressed.

Figure 3:
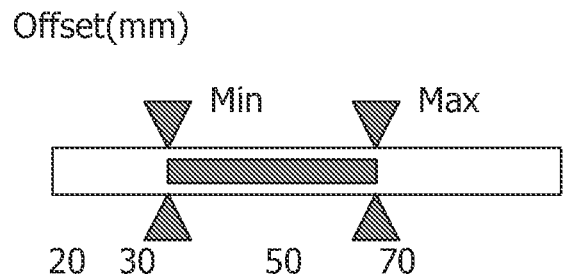
FIG. 3 shows an exemplary range editor for the range of the offset.

Alternatively, the dialog for selecting a discriminating characteristic may comprise three buttons. Upon pressing a button, a range editor for entering the range of a discriminating characteristic of the candidate hip-implant may be displayed. An exemplary range editor for the range of the offset is shown in FIG. 3.

In an embodiment of the system 100, the set of data-objects is a set of image data-objects. For example, each data-object may comprise a medical image and a diagnosis. Each data-object may further comprise additional information such as, but not limited to, image acquisition modality, patient age and patient sex. The set of image data-objects, organized as a relational database, for example, may be useful for a user, such as an oncologist or a brain surgeon, in assisting the user in diagnosing a new medical image. The new medical image may be a reference data-object and may be obtained by the system 100. The user determines an initial diagnosis, based on the new medical image. The query composed by the composition unit 110 may comprise this initial diagnosis. The query may further comprise additional information such as image acquisition modality, patient age and patient sex. The identification unit 120 of the system 100 is arranged to identify candidate images, based on the query. The presentation unit 130 presents candidate images to the user. The user may select a candidate image for providing user feedback on the selected candidate image. The discriminating characteristics may depend on the initial diagnosis. For example, in the case of a brain stroke, the discriminating characteristics may be the size of the stroke area, the location relative to a set of landmarks, and the average intensity of the stroke area. For example, in a fluid attenuation inversion recovery (FLAIR) image of the brain, the image is bright in areas where a stroke occurred some time ago, medium dark in areas where stroke can occur or recently occurred, and dark in areas where stroke cannot occur. Looking at the new medical image and at the candidate image, the user may provide the feedback unit 140 with clues on the discriminating characteristics. For example, the user feedback may comprise information that the affected area in the candidate image is too small and too bright. This feedback may then be used by the update unit 150 to update the query. The location and the size of the affected area in the candidate image may be computed by the computation unit 135 or may be comprised in the data-object. After a successful search, the identified certain data-object comprises a medical image showing a brain stroke area similar to the new medical image. The user may now retrieve and study the case history corresponding to and optionally comprised in the certain data-object. This may be helpful in deciding on the patient's final diagnosis, prognosis and treatment, for example.

The skilled person will understand that the system 100 according to the invention may be a valuable tool for assisting a physician in various tasks such as, but not limited to, medical diagnosing, prognosing and therapy planning The skilled person will further understand that other embodiments of the system 100 are also possible. It is possible, among other things, to redefine the units of the system and to redistribute their functions. For example, the registration unit 125, the presentation unit, and/or the feedback unit 140 may be combined into one unit. In an embodiment of the system 100, there can be a plurality of computation units replacing the computation unit 135. Each computation unit of the plurality of computation units may be arranged to compute a value of a predetermined parameter describing a data-object.

The units of the system 100 may be implemented using a processor. Normally, their functions are performed under control of a software program product. During execution, the software program product is normally loaded into a memory, like a RAM, and executed from there. The program may be loaded from a background memory, like a ROM, hard disk, or a magnetic and/or optical storage means, or may be loaded via a network like the Internet. Optionally, an application-specific integrated circuit may provide the described functionality.

Figure 4:
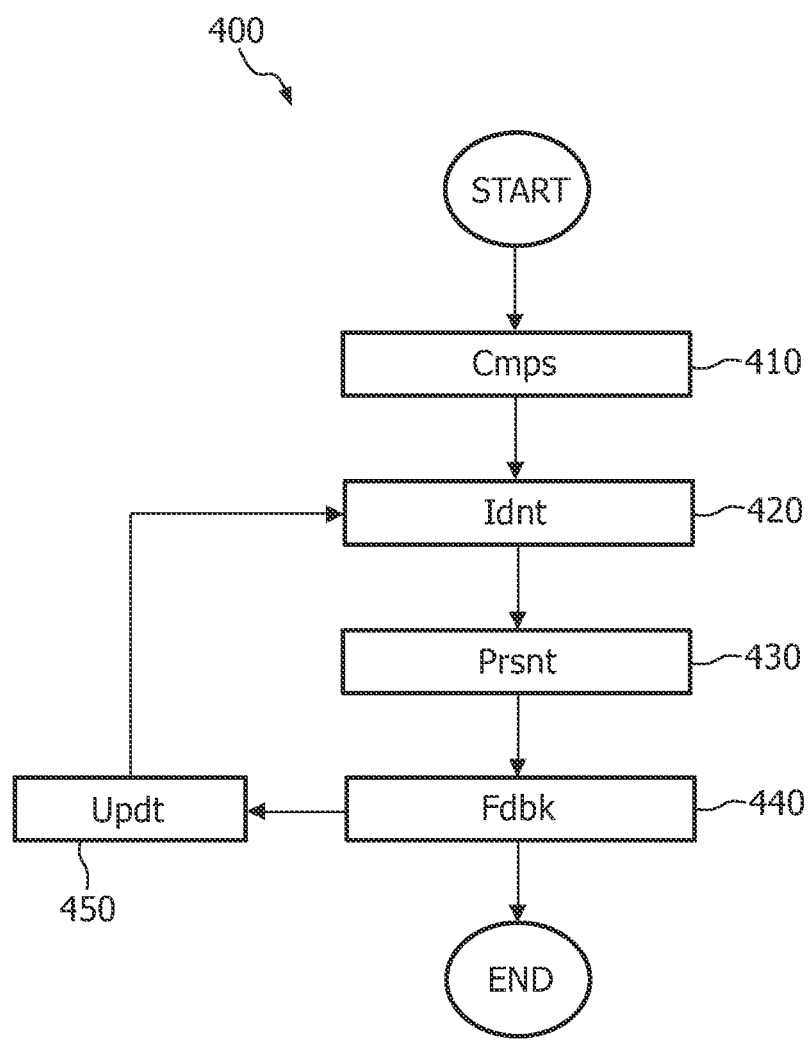
FIG. 4 shows a flowchart of an exemplary implementation of the method.

FIG. 4 shows a flowchart of an exemplary implementation of the method 400 of identifying a certain data-object of a set of data-objects, wherein each data-object of the set of data-objects is described by a plurality of discriminating characteristics. In a simple implementation, the method 400 has five steps. The method 400 begins with a composition step 410 for composing a query for identifying the certain data-object. After the composition step 410, the method 400 continues to an identification step 420 for identifying a candidate data-object of the set of data-objects, based on the query. After the identification step 420, the method 400 continues to a presentation step 430 for presenting a description of the candidate data-object to a user. After the presentation step 430, the method 400 continues to feedback step 440 for receiving user feedback on a discriminating characteristic of the plurality of discriminating characteristics, the discriminating characteristic describing the candidate data-object. If the user accepts the identified candidate data-object as the certain data-object, the method 400 terminates. If the user rejects the identified candidate data-object as the certain data-object, the method 400 may continue to an update step 450 for updating the query for identifying the certain data-object, based on the user feedback on the discriminating characteristic describing the candidate data-object. Alternatively, the method 400 may terminate without identifying the certain data-object e.g. based on a user input for terminating the method 400.

The order of steps in the method 400 is not mandatory, the skilled person may change the order of some steps or perform some steps concurrently using threading models, multi-processor systems or multiple processes without departing from the concept as intended by the present invention. Optionally, two or more steps of the method 400 of the current invention may be combined into one step. Optionally, a step of the method 400 of the current invention may be split into a plurality of steps.

Figure 5:
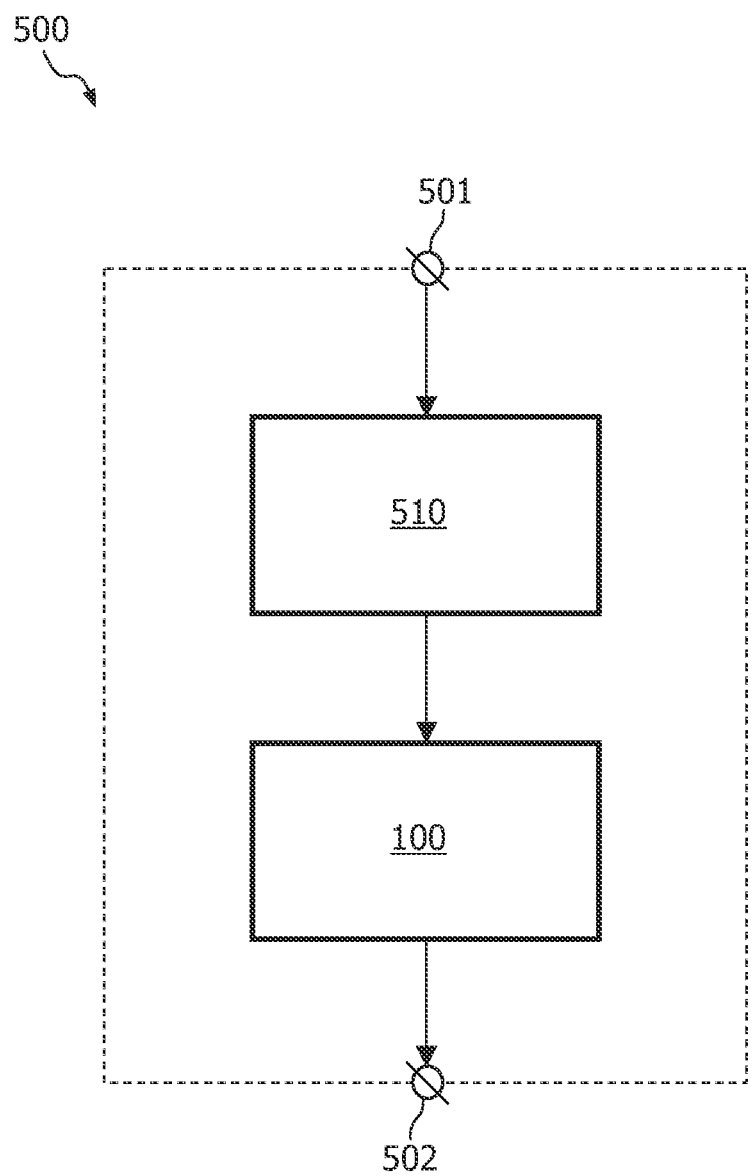
FIG. 5 schematically shows an exemplary embodiment of the image acquisition apparatus.

FIG. 5 schematically shows an exemplary embodiment of the image acquisition apparatus 500 employing the system 100, said image acquisition apparatus 500 comprising an image acquisition unit 510 connected via an internal connection with the system 100, an input connector 501, and an output connector 502. This arrangement advantageously increases the capabilities of the image acquisition apparatus 500, providing said image acquisition apparatus 500 with advantageous capabilities of the system 100 for identifying a certain data-object of a set of data-objects, each data-object of the set of data-objects being described by a plurality of discriminating characteristics. Examples of image acquisition apparatus comprise, but are not limited to, a CT system, an X-ray system, an MRI system, an US system, a PET system, a SPECT system, and a NM system.

Figure 6:
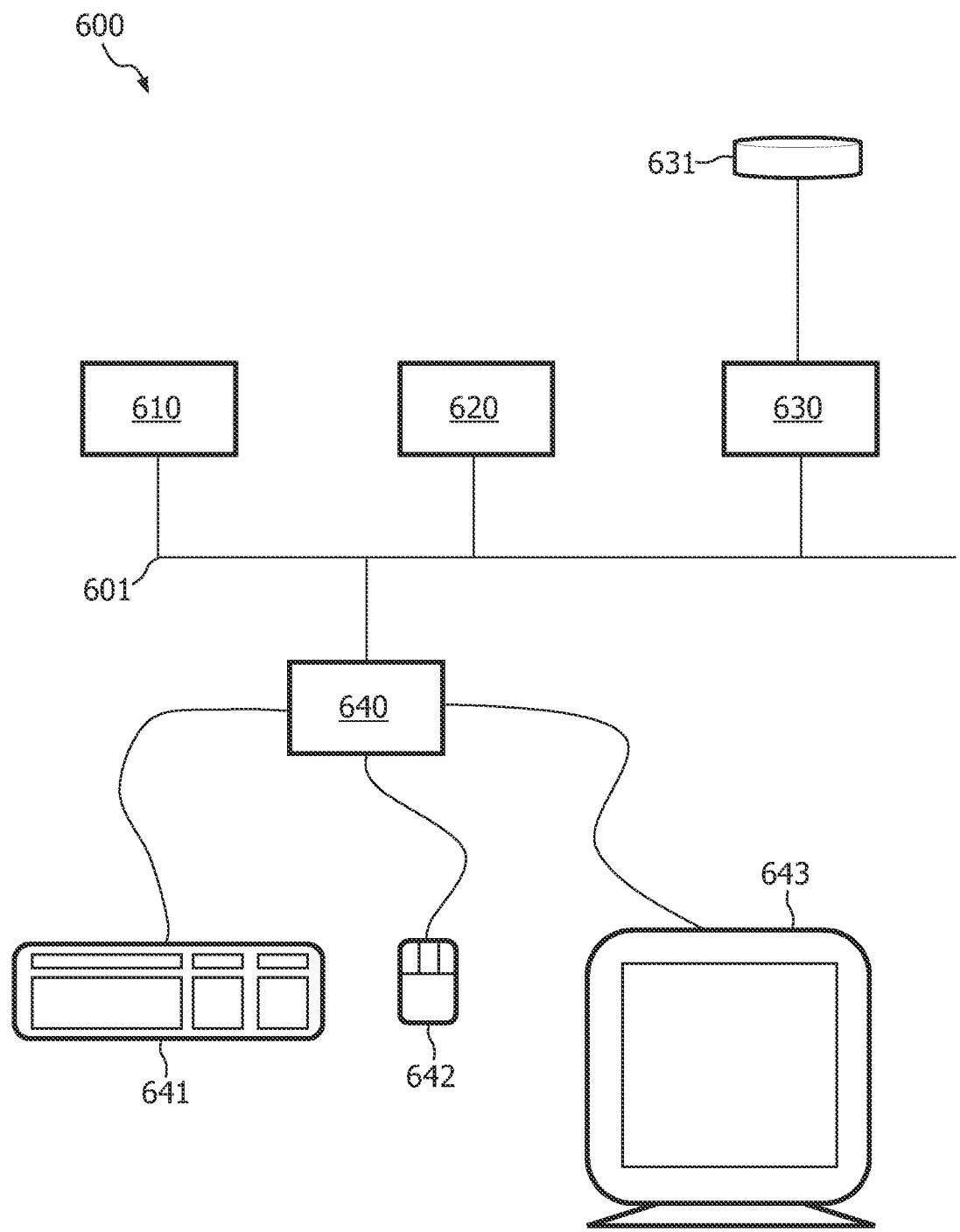
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. The skilled person will understand that numerous other embodiments of the workstation 600 are known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera does not indicate any ordering. These words are to be interpreted as names.

The invention claimed is:

1. A system for identifying a certain data-object of a set of data-objects stored in associated memory, wherein each data-object of the set of data-objects is described by a plurality of discriminating characteristics; the system comprising:
a user input device operable to input a query for identifying the certain data-object;
a processor operable to identify a candidate data-object of the set of data-objects, used on the query;
a display operable to display a description of the candidate data-object to a user;
a user interface operable to receive user feedback on a discriminating characteristic of the plurality of discriminating characteristics, the discriminating characteristic describing the candidate data-object, wherein the user feedback includes a reason for accepting or rejecting the candidate data-object associated with the discriminating characteristic; and
the processor operable to update the query for identifying the certain data-object, based on the user feedback on the mason associated with the discriminating characteristic describing the candidate data-object in relation to the discriminating characteristic describing each other data-object of the set of date-objects.

2. A system as claimed in claim 1, wherein the user interface is further arranged for requesting use feedback on the discriminating characteristics describing the candidate data-object.

3. A system as claimed in claim 1, further comprising a reference unit for receiving a reference data-object.

4. A system as claimed in claim 3, further comprising is registration unit for registering the candidate data-object with the reference data-object.

5. A system as claimed in claim 1, further comprising a computation unit for computing a value of a parameter describing the candidate data-object.

6. A system as claimed in claim 1, wherein the set of data-objects is a set of implant data-objects.

7. A system as claimed in claim 1, wherein the set of data-objects is a set of image data-objects.

8. The system of claim 7, further comprising an image acquisition unit for acquisition of image data-objects.

9. A method of identifying a certain data-object of a et of data-objects, wherein each data-object of the set of data-objects is described by a plurality of discriminating characteristics, the method comprising:
  composing a query for identifying the certain data-object, with one or more computers, identifying a candidate data-object of the set of data-objects, based on the query,
  presenting a description of the candidate data-object to a user;
  receiving user feedback on a discriminating characteristic of the plurality of discriminating characteristics, the discriminating characteristic describing a value associated with the candidate data-object, wherein the use feedback includes a selection of a reason for accepting or rejecting the candidate data-object associated with the discriminating characteristic from among a plurality of graphical representations of reasons, the reason corresponding to whether a value of the discriminating characteristic of the certain data-Object is greater than or smaller than the value of the discriminating characteristic of the candidate data-object; and
  with one or more computers, updating the query for identifying the certain data-object, based on the user feedback on the selected reason associated with the discriminating characteristic describing the candidate data-object.

10. A non-transitory computer readable medium carrying software which controls one or more computers to perform the method according to claim 9.

11. The system of claim 8, wherein the image acquisition apparatus is a CT system, an X-ray system, an MRI system, a US system, a PET system, a SPECT system or an NM system.

12. The system of claim 1, wherein the user interface is further operable to receive it syntactically correct user input.

13. The system of claim 5, wherein the computed value is a value of the discriminating characteristic, and the user feedback further comprises a modification of the value of the discriminating characteristic.

14. A system for identifying a certain data-object of a set of data-objects stored in associated memory, wherein well data-object of the set of data-objects is described, by a plurality of discriminating characteristics, the system comprising:
  a user input device operable to input a query for identifying the certain data-object;
  a processor operable to identify a candidate data-object of the set of data-objects, based on the query;
  a display operable to display a description of the candidate data-object to a user;
  a user interface operable to receive user feedback on a discriminating characteristic of the plurality of discriminating characteristics, the discriminating characteristic describing the candidate data-object, Wherein the user feedback includes a reason for accepting or rejecting the candidate data-object associated with the discriminating characteristic, the reason for accepting or rejecting the candidate data-object is selected from among a plurality of graphical representations of reasons displayed on the display;
  a computation unit for computing a value of the candidate data-object; and
  the processor operable to update the query for identifying the certain data-object, based on the user feedback on the reason associated with the discriminating characteristic describing the candidate data-object,
  wherein the user interface is operable to receive use feedback on whether a value of the discriminating characteristic of the certain data-object is greater than or smaller than the value of the discriminating characteristic of the candidate data-object.

15. The system of claim 1, wherein the user interface further comprises a dialog including a first region and a second region, the first region displaying values of discriminating characteristics associated with the candidate data-object, and the second region displaying a visual representation of the candidate data-object.

16. The system of claim 15, wherein the user interface further comprises at least one graphical representation of at least one reason associated with rejection of the candidate data-object, and wherein the used feedback is received in accordance with a selection thereof.

17. The system of claim 16, wherein the at least one graphical representation of at least one reason includes an associated number of candidate data-objects in the set corresponding thereto.

18. The method of claim 9, further comprising:
  computing, with the one or more computers, a value associated with the discriminating characteristic in accordance with received user feedback; and
  updating the query based on the computed value of the discriminating characteristic.

19. The method of claim 18, wherein the user feedback further comprises modifying of the value of the discriminating characteristic.

20. The system of claim 13, wherein the user Interface is operable to receive user feedback on whether a value of the discriminating characteristic of the certain data-object is greater than or smaller than the value of the discriminating characteristic of the candidate data-object.

* * * * *